United States Patent
Ostermann et al.

(10) Patent No.: US 9,128,067 B2
(45) Date of Patent: Sep. 8, 2015

(54) TEST STATION FOR PORTABLE GAS MEASURING DEVICES

(71) Applicant: Dräger Safety AG & Co. KGaA, Lübeck (DE)

(72) Inventors: Ulf Ostermann, Rümpel (DE); Ingo Kaneblei, Lübeck (DE); Stefan Barten, Lübeck (DE); Christof Möller, Lübeck (DE); Sven Schimmel, Bad Schwartau (DE)

(73) Assignee: Dräger Safety AG & Co. KGaA, Lübeck (DE)

( * ) Notice: Subject to any disclaimer, the term of this patent is extended or adjusted under 35 U.S.C. 154(b) by 0 days.

(21) Appl. No.: 14/376,743

(22) PCT Filed: Jun. 10, 2013

(86) PCT No.: PCT/EP2013/061916
§ 371 (c)(1),
(2) Date: Aug. 5, 2014

(87) PCT Pub. No.: WO2013/186171
PCT Pub. Date: Dec. 19, 2013

(65) Prior Publication Data
US 2015/0020569 A1    Jan. 22, 2015

(30) Foreign Application Priority Data
Jun. 15, 2012 (DE) .......... 10 2012 210 090

(51) Int. Cl.
*G01N 21/00* (2006.01)
*G01N 33/00* (2006.01)

(52) U.S. Cl.
CPC ........ *G01N 33/0006* (2013.01); *G01N 33/0004* (2013.01); *G01N 33/007* (2013.01)

(58) Field of Classification Search
CPC .......... G01N 33/0006; G01N 33/007
USPC .......... 73/1.06
See application file for complete search history.

(56) References Cited

U.S. PATENT DOCUMENTS 6,442,639 B1    8/2002   McElhattan et al.
7,530,255 B2    5/2009   Frank et al.

FOREIGN PATENT DOCUMENTS

JP    2006 003 115 A    1/2006
WO    01/82 063 A1    11/2001

OTHER PUBLICATIONS

Dräger E-Cal station, Instructions for Use, 1st Edition, Sep. 2005.
(Continued)

*Primary Examiner* — Hezron E Williams
*Assistant Examiner* — Rodney T Frank
(74) *Attorney, Agent, or Firm* — McGlew & Tuttle, P.C.

(57) ABSTRACT

A test station for a plurality of test gases, includes a main unit (10) with a control (12) and test modules (20), each for a gas measurement device, that exchange data to register a type of gas measurement device and test gas(es) required for the device type. The control sets a schedule for a test using a test gas, or for a plurality of successive tests each with different test gases and carries out the specific test planned according to the schedule, in parallel with tests for all of the test modules for a test gas and determines, as an additional gas measurement device is inserted, based on the particular device type of the additional gas measurement device, whether the currently-running test with the current test gas is suitable for the inserted test module; and if the test gas is suitable, to start the test for this test module.

15 Claims, 4 Drawing Sheets

(56) References Cited

OTHER PUBLICATIONS

MSA Instrument Division: "Galaxy Automated Test System User Manual", Internet Citation, 2003, XP002375025: http://media.msanet.com/NA/USA/PortableInstruments/CalibrationEquipment/GalaxyAutomatedTestSystem/10061049.pdf [retrieved on Mar. 30, 2006] p. 1-p. 9.

Daniel Wojtowicz: "Microdock II User Manual", Internet Citation, Jan. 13, 2005, XP002375024: http://www.gasmonitors.com/main.cfm?sub3=216&page=pdf&page=pdf&doc=2&pid=34 [retrieved on Mar. 30, 2006] the whole document.

| Module 1 | | Module 2 | | Module 3 | |
| --- | --- | --- | --- | --- | --- |
| Status | Action | Status | Action | Status | Action |
| Device a Required<br><br>Gas A<br>Gas B<br>Gas D | Gas A | | | | |
| | | Device b Required<br><br>Gas A<br>Gas B<br>Gas C | Gas A | | |
| | Gas B | | | Device c Required<br><br>Gas A<br>Gas B<br>Gas C | Gas A |
| | | | Gas B | | Gas B |
| | Gas D | | | | |
| | | | Gas C | | Gas C |
| Device d Required<br><br>Gas A<br>Gas B<br>Gas C | Gas C | | | | |
| | Gas A | Device e Required<br><br>Gas A<br>Gas B | Gas A | Device f Required<br><br>Gas A<br>Gas B | Gas A |
| | Gas B | | Gas B | | Gas B |

Fig. 2

| Module 1 | | Module 2 | | Module 3 | |
|---|---|---|---|---|---|
| Status | Action | Status | Action | Status | Action |
| Device a Required  Gas A Gas B Gas D | Gas A | | | | |
| | | Device b Required  Gas A Gas B Gas C | Gas A | Device c Required  Gas A Gas B Gas C | Gas A |
| | Gas B | | Gas B | | Gas B |
| | | | Gas C | | Gas C |
| | Gas D | | | | |
| | | Device e Required  Gas A Gas B | Gas A | | |
| Device d Required  Gas A Gas B Gas C | Gas A | | | Device f Required  Gas A Gas B | Gas A |
| | Gas B | | Gas B | | Gas B |
| | Gas C | | | | |

Fig. 3

| Module 1 | | Module 2 | | Module 3 | |
|---|---|---|---|---|---|
| Status | Action | Status | Action | Status | Action |
| Device a Required<br><br>Gas A<br>Gas B<br>Gas D | Gas A<br><br>Gas B<br><br>Gas D | Device b Required<br><br>Gas A<br>Gas B<br>Gas C | Gas A<br><br>Gas B<br><br>Gas C | Device c Required<br><br>Gas A<br>Gas B<br>Gas C | |
| Device d Required<br><br>Gas A<br>Gas B<br>Gas C | | | | | Gas C<br><br>Gas A<br><br>Gas B |
| | | Device e Required<br><br>Gas A<br>Gas B | | | |
| | Gas B<br><br>Gas A<br><br>Gas C | | | Device f Required<br><br>Gas A<br>Gas B | |

TEST STATION FOR PORTABLE GAS MEASURING DEVICES

CROSS REFERENCE TO RELATED APPLICATIONS

This application is a United States National Phase Application of International Application PCT/EP2013/061916 filed Jun. 10, 2013 and claims the benefit of priority under 35 U.S.C. §119 of German Patent Application DE 10 2012 210 090.3 filed Jun. 15, 2012, the entire contents of which are incorporated herein by reference.

FIELD OF THE INVENTION

The present invention pertains to a test station for portable gas measuring devices for a plurality of test gases, comprising a main unit including a control and analysis unit, and comprising a plurality of test modules connected to the main unit for the purpose of exchanging data, into each of which a gas measuring device can be inserted for testing, whereby means are provided for detecting the type of the respective gas measuring device that has been inserted into a test module and for determining the test gas or test gases required for this type of device, and whereby the main unit comprises a plurality of gas inlets for different test gases, whereby, under the control of the control and analysis unit, the test gas is conducted to the test modules from a selected gas inlet by means of a gas line.

BACKGROUND OF THE INVENTION

Many kinds of portable gas measuring devices are known, which must be carried by persons, who are in areas, in which they may be exposed to harmful gases. Such portable gas measuring devices must be routinely tested for their operability, i.e., whether they react at all to the test gas or test gases to be detected by them. Besides such a mere operating test, test gas with a known concentration can be fed to the gas measuring device in a calibrating station in order to adjust the test signal of the gas measuring device.

A test station of the type mentioned in the introduction is the Dräger E-Cal station. This station is a calibrating station with a modular design for the automatic adjustment and for automatic operating tests of portable gas measuring devices. The test station comprises a main unit, including a control and analysis unit (for example, a PC). Further, a plurality of test modules connected to the main unit for the purpose of exchanging data are present, into which each gas measuring device can be inserted for testing. Means are provided for detecting the type of the respective gas measuring device that has been inserted into a test module and for determining therefrom the test gas or test gases required for this device type. The main unit comprises a plurality of gas inlets for different test gases. Under the control of the control and analysis unit, each test gas is conducted from a selected gas inlet in a common gas line, to which all test modules are connected. In the prior-art station, tests are controlled centrally by the main unit. In this case, the main unit controls the test schedule, such that first the test module, into which a gas measuring device is the first to have been inserted, is processed. A plurality of gas measuring devices may also be inserted at the same time into a plurality of test modules and the tests are then started centrally at the main unit, after which all gas measuring devices that require a defined test gas are supplied with this test gas in parallel.

Test stations for gas measuring devices, into which a plurality of gas measuring devices of the same type can be inserted, which are then supplied in parallel with the same test gas or the same test gas sequence and are tested in parallel, are also known from JP 2006 003 115 A and U.S. Pat. No. 7,530,255 B2.

In everyday operation, however, the situation frequently arises that a plurality of operators insert their gas measuring device into a test module chronologically one after the other and then want to have a test result as soon as possible. In this situation, in the test station according to the state of the art, first only the first gas measuring device inserted is tested and, then one gas measuring device after the other is separately tested in the sequence of their input.

In the processing of the first test module with the first gas measuring device, at first the type of the gas measuring device that has been inserted into the test module is detected. This may take place, for example, by reading out a memory in the gas measuring device, in which the device type is stored. Which test gases are required for each device type are also stored beforehand When, for example, the test gases A, B and C are required for the currently first inserted gas measuring device, then the main unit first selects the gas inlet for the test gas A and conducts it further to the test modules by means of the common gas line, after which one proceeds with test gas B and finally with test gas C until all the tests have been carried out for the gas measuring device inserted first into the test module. Then, the main unit proceeds with the processing of that test module, into which the next gas measuring device has been inserted after the first one. In this case, a plurality of other gas measuring devices may also have already been inserted into test modules during the testing for the gas measuring device in the one test module. These gas measuring devices are then chronologically successively processed one after the other, whereby each of the test gases are fed to a gas measuring device in a test module in accordance with the test gases required for this device type. The sequence of the processing of the test modules with inserted gas measuring devices takes place according to the chronological sequence of the insertion of the gas measuring devices into the respective test modules.

The prior-art test station can still be improved for certain usage situations, because in the situation, in which an operator is faced with a gas measuring device at the test station and has inserted his gas measuring device into a test module and the testing for this gas measuring device has been started by the main unit, another operator may insert the operator's gas measuring device into another test module, but the testing for this other test module may only be started by the main unit after conclusion of the test for the first gas measuring device. In such a situation, or when still other operators want to use the test station at different times, only one gas measuring device is tested at a time. Moreover, the test gases, which are fed by means of the common gas line, are each only used for one gas measuring device in one test module in such situations.

SUMMARY OF THE INVENTION

An object of the present invention is to improve a test station for portable gas measuring devices of the type mentioned in the introduction, such that tests on a plurality of gas measuring devices, which have been inserted into test modules one after the other and whose tests have started one after the other, can be carried out more rapidly. Further, the consumption of test gas shall be reduced in such cases.

According to the present invention, the control and analysis unit is set up (configured) to set a schedule for a test with a test gas or for successive tests to be carried out each with different test gases in accordance with the device types currently determined in the test modules, and then to carry out each test planned according to the schedule with the associated test gas in parallel for all the test modules, for which the current test gas is suitable in accordance with the type of gas measuring device that has been inserted, and to determine, as soon as another gas measuring device has been inserted into a test module and is reported as being ready for testing, in accordance with the respective type of the other gas measuring device, whether the currently running test with the current test gas is suitable for the inserted gas measuring device and if the test gas is suitable, to start the test for this test module as well.

Because of the parallel processing of a plurality of test modules at the same time, a plurality of gas measuring devices can be tested more rapidly, since their processing can take place in parallel and not in succession as in the state of the art. Further, the consumption of test gases is reduced, since each test gas fed through the common gas line for a plurality of test modules can be used at the same time. In addition, the carrier of the gas measuring device can initiate the test independently of the main unit in a decentralized manner directly at the test module used by him; the test then begins as soon as a test gas suitable for the gas measuring device is present and the control and analysis unit releases the feed from the gas line to the test module.

In an advantageous embodiment, the control and analysis unit can, when setting the schedule, be set up to select such a sequence of test gases that apply to the type of gas measuring device currently inserted into the test station for the longest time, but still untested. As an alternative, the control and analysis unit can, when setting the schedule, be set up to select the sequence of each test gas, such that the tests with the respective test gases can currently be carried out in parallel for a maximum number of inserted gas measuring devices.

In an advantageous embodiment, the control and analysis unit can be further set up to determine from the test gas sequence planned for a gas measuring device in a test module according to preset criteria whether adverse interactions are predetermined as known for a direct sequence of two test gases following each other, and if so, to carry out a flushing phase between the feeds of the two test gases at the test module in question.

In an advantageous embodiment, the test modules can be set up to report the test module as being ready for testing to the control and analysis unit, when, after inserting a gas measuring device into the respective test module, (I) a flap at the test module is closed, (ii) a manual operation is carried out at the gas measuring device, (iii) a manual operation at the test module is carried out, or (iv) a sensor indicates a gas measuring device has been inserted into the test module.

In this way, the carrier of the gas measuring device can pick up this gas measuring device and insert it into a free test module and then initiate the display of the readiness for testing to the control and analysis unit locally at the test module in order to thus release the test for the inserted gas measuring device in a decentralized manner.

In a preferred embodiment, the present invention creates a calibrating station comprising a test station for portable gas measuring devices as described above and comprising means for feeding test gases in preset concentrations.

The present invention is described below on the basis of exemplary embodiments and in connection with the figures. The various features of novelty which characterize the invention are pointed out with particularity in the claims annexed to and forming a part of this disclosure. For a better understanding of the invention, its operating advantages and specific objects attained by its uses, reference is made to the accompanying drawings and descriptive matter in which preferred embodiments of the invention are illustrated.

BRIEF DESCRIPTION OF THE DRAWINGS

In the drawings:

FIG. 2 is a view showing a schedule for the parallel carrying out of tests comprising a testing device according to a first embodiment;

FIG. 3 is a view showing a schedule for the parallel carrying out of tests comprising a testing device according to a second embodiment; and FIG. 4 is a view showing a schedule for the parallel carrying out of tests with a test station from the state of the art.

DESCRIPTION OF THE PREFERRED EMBODIMENTS

Figure 1:
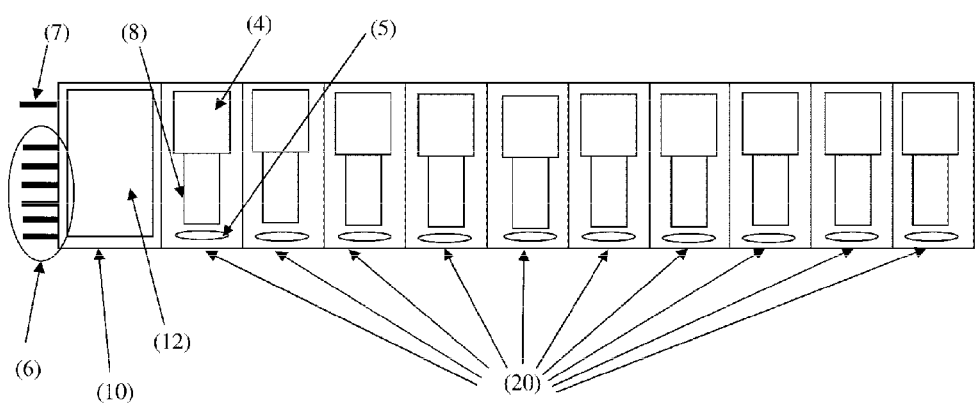
FIG. 1 is a schematic block diagram of a test station.

Referring to the drawings in particular, the test station schematically shown in FIG. 1 comprises a main unit 10 and ten test modules 20 in this exemplary embodiment. The main unit 10 is connected to the test modules 20 by means of a bidirectional data link for the purpose of exchanging data. Further, a common gas line leads out of the main unit 10 to the test modules; the test modules 20 are connected in parallel to the gas line and are each provided with valve means, which, controlled by the main unit 10, open or close the flow of test gas from the gas line to the individual test module.

In the exemplary embodiment shown, six gas inlets 6 for different test gases are provided at the main unit 10. After selecting one of the gas inlets 6, the common gas line is supplied with the selected test gas. The test gas is again discharged to the outside by means of the waste gas line 7.

When a gas measuring device 8 is inserted into one of the test modules 20 and the flap 4 is closed, a control and analysis unit 12 of the main unit 10 starts with checking whether the test or calibration for the inserted gas measuring device 8 is possible with the gases present at the gas inlets 6 and whether the gas measuring device 8 is ready for testing. If all prerequisites for the carrying out of the test or calibrating procedure are met, a schedule is set for the tests to be carried out with consideration of possible running tests and of the gas measuring devices 8 already inserted into other test modules, which are also waiting for the start of a test. Different strategies are possible for setting the schedule. FIGS. 2 and 3 show two possible algorithms for setting the schedule.

In the approach for setting the schedule shown in FIG. 2, the "oldest" inserted gas measuring device determines the test gas sequence. I.e., the first gas measuring device inserted into a test module 20 after switching on the test station determines the beginning of the schedule by means of the sequence of test gases required for this gas measuring device. A gas measuring device a is inserted into a test module 1 in the example shown in FIG. 2. This gas measuring device requires the test gases A, B and D. FIG. 2 then shows for the device a in the "action" column lying next to it that the test gases A, B and D are fed one after the other to the test module with the device a.

A little after inserting device a, a device b is inserted into the test module 2. This device b requires the test gases A, B and C. Since the test gases A and B are required both by device a and device b, the test gases A and B can be fed in parallel to the test module 1 and test module 2. FIG. 3 further shows that another gas measuring device c is inserted into a test module 3 after device b. This device c also requires the test gases A, B and C. These test gases may be fed to the device c in the test module 3 in parallel to the device b in the test module 2. Still before completing the feeding of the test gas C to the device c in test module 3, another device d is inserted into the test module 1, which requires the test gases A, B and C. Since the test gas C is still being used for the tests of device b in test module 2 and device c in test module 3, the test on device d starts in parallel thereto with the feeding of the test gas C to the test module 1. Further, FIG. 2 also shows that later another device e and a device f are inserted into the test module 2 and test module 3, which require the test gases A and B. The tests with the feeding of the test gases A and B are carried out in parallel for the devices d, e and f.

An alternative for setting the schedule is shown in FIG. 3 with identical manner of representation as in FIG. 2. In this case, the schedule of test gases is set by selecting the gas presently required by the most modules as test gas to be the next one and by the test being carried out therewith.

The parallel carrying out of tests shown in FIGS. 2 and 3 with a test station according to the present invention requires approximately the same time for carrying out pending tests. FIG. 4 shows, for comparison, a test sequence for identical gas measuring devices and identical chronological sequence of inserting the gas measuring devices as in FIGS. 2 and 3, whereby the test sequence takes place in a centrally controlled manner here one after the other as in the state of the art. In this case, namely the device a is inserted as the first one and supplied with the test gases A, B and D. The test for device b inserted into test module 2 begins only after completion of the test for device a. It can be recognized that device b has a certain waiting time until the test for device a in test module 1 is completed. The feeding of the test gases A, B and C to device b in test module 2 begins only after that. During this test for device b in test module 2, a device d in test module 1 and a device c in test module 3, etc. are, in turn, waiting. A comparison of the test sequence according to the state of the art as in FIG. 4 with the test sequences of a test station according to the present invention as shown in FIG. 2 or 3 makes it clear that parallel processing in the test station according to the present invention makes possible a marked acceleration of carrying out tests for a plurality of test measuring devices.

In this way, it is possible for a plurality of operators with different gas measuring devices to carry out tests at different test modules. The test starts, for example, automatically by closing the flap 4, and no further adjustments of the main unit 10 have to be made by the operators. A response is displayed on a display of the main unit 10 separately via the output of the test for each test module 20. At the same time, a status LED 5 at each test module 20 also gives a direct optical response via the output of the test. Due to the parallel supplying of the individual test modules 20 by means of a central, common gas line, gas measuring devices with identical equipment can be tested chronologically independently of one another, both at the same time and at different times, in the test modules. In this case, in particular, a considerable saving of time in the testing of many devices is achieved compared to conventional test stations.

Due to the design of the test station according to the present invention a central sequential control and a central storage of the results of the tests are possible. At the same time, there is a high variability for the independent operation of test measurements in the individual test modules. Thus, a rapid test time and a high throughput of gas measuring devices to be tested is possible. A savings of test gas is also achieved due to the feeding of gas to a plurality of test modules at the same time.

While specific embodiments of the invention have been shown and described in detail to illustrate the application of the principles of the invention, it will be understood that the invention may be embodied otherwise without departing from such principles.

The invention claimed is:

1. A test station for portable gas measuring devices for a plurality of test gases, the test station comprising:
    a main unit comprising a control and analysis unit and a plurality of gas inlets, each of the inlets for one of different test gases;
    a gas line; and
    a plurality of test modules, each of the test modules being connected to the main unit and exchanging data with the main unit, into each of which a gas measuring device can be inserted for testing, detecting a type of gas measuring device that has been inserted into the test module and determining therefrom a test gas or test gases required for the detected type of device, whereby, under the control of the control and analysis unit, the test gas is conducted by means of the gas line to the test modules from a selected gas inlet, wherein the control and analysis unit is configured to set a schedule for a test with a test gas or a plurality of successive tests to be carried out each with different test gases in accordance with the device types currently determined in the test modules, and then to carry out each test planned according to the schedule with the associated test gas in parallel with the test for all test modules, for which the current test gas is suitable in accordance with the type of gas measuring device that has been inserted, and to determine, as soon as another gas measuring device is inserted into the test module and is reported as being ready for testing, in accordance with the respective type of the other gas measuring device, whether the currently running test with the current test gas is suitable for the inserted gas measuring device, and if the test gas is suitable, to start the test for this another test module.

2. A test station in accordance with claim 1, wherein the control and analysis unit is configured, when setting the schedule, to select the sequence of test gases that apply to the type of gas measuring device currently inserted into the test station for the longest time, but still untested.

3. A test station in accordance with claim 2, wherein the control and analysis unit is configured, when setting the schedule, to select the sequence of each test gas, such that the test with the respective test gas can currently be carried out in parallel for a maximum number of inserted gas measuring devices.

4. A test station in accordance with claim 1 wherein the control and analysis unit is further configured to determine, from the test gas sequence planned for a gas measuring device in a test module according to preset criteria, whether adverse interactions are predetermined as known for a direct sequence of two test gases following each other, and if so, to carry out a flushing phase between the feeds of the two test gases at the test module in question.

5. A test station in accordance with claim 1 wherein the test modules are configured to report the test module as being ready for testing to the control and analysis unit, when, after inserting a gas measuring device into the respective test module, (I) a flap at the test module is closed, (ii) a manual operation is carried out at the gas measuring device, (iii) a manual operation is carried out at the test module, or (iv) a sensor indicates a gas measuring device has been inserted into the test module.

6. A test station in accordance with claim 1, wherein the test station is a calibrating station further comprising a means for feeding test gases in predetermined concentrations.

7. A test station in accordance with claim 2, wherein the control and analysis unit is further configured to determine, from the test gas sequence planned for a gas measuring device in a test module according to preset criteria, whether adverse interactions are predetermined as known for a direct sequence of two test gases following each other, and if so, to carry out a flushing phase between the feeds of the two test gases at the test module in question.

8. A test station in accordance with claim 3, wherein the control and analysis unit is further configured to determine, from the test gas sequence planned for a gas measuring device in a test module according to preset criteria, whether adverse interactions are predetermined as known for a direct sequence of two test gases following each other, and if so, to carry out a flushing phase between the feeds of the two test gases at the test module in question.

9. A test station in accordance with claim 2, wherein the test modules configured to report the test module as being ready for testing to the control and analysis unit, when, after inserting a gas measuring device into the respective test module, (I) a flap at the test module is closed, (ii) a manual operation is carried out at the gas measuring device, (iii) a manual operation is carried out at the test module, or (iv) a sensor indicates a gas measuring device has been inserted into the test module.

10. A test station in accordance with claim 3, wherein the test modules configured to report the test module as being ready for testing to the control and analysis unit, when, after inserting a gas measuring device into the respective test module, (I) a flap at the test module is closed, (ii) a manual operation is carried out at the gas measuring device, (iii) a manual operation is carried out at the test module, or (iv) a sensor indicates a gas measuring device has been inserted into the test module.

11. A calibrating station comprising:
a main unit comprising a control and analysis unit and a plurality of gas inlets, each of the inlets for one of different test gases;
a gas line;
a plurality of test modules, each of the test modules being connected to the main unit and exchanging data with the main unit, into each of which a gas measuring device can be inserted for testing, detecting a type of gas measuring device that has been inserted into the test module and determining therefrom a test gas or test gases required for the detected type of device, whereby, under the control of the control and analysis unit, the test gas is conducted by means of the gas line to the test modules from a selected gas inlet, wherein the control and analysis unit is configured to set a schedule for a test with a test gas or a plurality of successive tests to be carried out each with different test gases in accordance with the device types currently determined in the test modules, and then to carry out each test planned according to the schedule with the associated test gas in parallel with the test for all test modules, for which the current test gas is suitable in accordance with the type of gas measuring device that has been inserted, and to determine, as soon as another gas measuring device is inserted into the test module and is reported as being ready for testing, in accordance with the respective type of the other gas measuring device, whether the currently running test with the current test gas is suitable for the inserted gas measuring device, and if the test gas is suitable, to start the test for this another test module; and
a means for feeding test gases in predetermined concentrations.

12. A calibrating station in accordance with claim 11, wherein the control and analysis unit is configured, when setting the schedule, to select the sequence of test gases that apply to the type of gas measuring device currently inserted into the test station for the longest time, but still untested.

13. A calibrating station in accordance with claim 12, wherein the control and analysis unit is configured, when setting the schedule, to select the sequence of each test gas, such that the test with the respective test gas can currently be carried out in parallel for a maximum number of inserted gas measuring devices.

14. A calibrating station in accordance with claim 11, wherein the control and analysis unit is further configured to determine, from the test gas sequence planned for a gas measuring device in a test module according to preset criteria, whether adverse interactions are predetermined as known for a direct sequence of two test gases following each other, and if so, to carry out a flushing phase between the feeds of the two test gases at the test module in question.

15. A calibrating station in accordance with claim 11, wherein the test modules configured to report the test module as being ready for testing to the control and analysis unit, when, after inserting a gas measuring device into the respective test module, (I) a flap at the test module is closed, (ii) a manual operation is carried out at the gas measuring device, (iii) a manual operation is carried out at the test module, or (iv) a sensor indicates a gas measuring device has been inserted into the test module.

* * * * *